(12) United States Patent
Perschbacher et al.

(10) Patent No.: US 7,970,463 B2
(45) Date of Patent: Jun. 28, 2011

(54) ANTI-TACHYARRHYTHMIA SYSTEM WITH UNIFIED ATRIAL TACHYARRHYTHMIA RATE THRESHOLD

(75) Inventors: David L. Perschbacher, Coon Rapids, MN (US); James O. Gilkerson, Stillwater, MN (US); James Kalgren, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 401 days.

(21) Appl. No.: 12/264,778

(22) Filed: Nov. 4, 2008

(65) Prior Publication Data

US 2009/0163966 A1 Jun. 25, 2009

Related U.S. Application Data

(60) Provisional application No. 61/009,065, filed on Dec. 20, 2007.

(51) Int. Cl.
*A61N 1/00* (2006.01)
*A61B 5/04* (2006.01)

(52) U.S. Cl. ............... 607/4; 607/5; 607/9; 600/515; 600/518

(58) Field of Classification Search .......... 607/4–5, 607/9, 11–12; 600/509, 513, 515–518
See application file for complete search history.

(56) References Cited

U.S. PATENT DOCUMENTS

| | | | |
|---|---|---|---|
| 5,755,736 A * | 5/1998 | Gillberg et al. | 607/4 |
| 6,496,731 B1 | 12/2002 | Lovett | |
| 7,194,300 B2 * | 3/2007 | Korzinov | 600/518 |
| 7,308,308 B1 | 12/2007 | Xi et al. | |
| 7,328,063 B2 * | 2/2008 | Zhang et al. | 600/515 |
| 7,623,911 B2 * | 11/2009 | Sarkar et al. | 600/510 |
| 7,840,265 B2 * | 11/2010 | Perschbacher et al. | 607/4 |
| 2002/0147472 A1 | 10/2002 | Seim et al. | |
| 2004/0116982 A1 | 6/2004 | Conley et al. | |
| 2005/0010258 A1 | 1/2005 | Peterson et al. | |
| 2005/0113705 A1 | 5/2005 | Fischell et al. | |
| 2009/0099616 A1 | 4/2009 | Li et al. | |

FOREIGN PATENT DOCUMENTS

WO   WO-2008/054261 A1   5/2008

OTHER PUBLICATIONS

"International Application Serial No. PCT/US2008/012458, International Search Report mailed Apr. 21, 2009", 5 pgs.
"International Application Serial No. PCT/US2008/012458, Written Opinion mailed Apr. 21, 2009", 8 pgs.

* cited by examiner

*Primary Examiner* — Niketa I Patel
*Assistant Examiner* — Catherine Voorhees
(74) *Attorney, Agent, or Firm* — Schwegman, Lundberg & Woessner, P.A.

(57) ABSTRACT

A cardiac rhythm management (CRM) system includes an implantable cardioverter defibrillator (ICD) and an external system. The ICD includes a plurality of functional modules performing tachyarrhythmia classification and therapy control functions using atrial tachyarrhythmia rate thresholds that are set to a unified value. In one embodiment, the CRM system allows a user to activate and deactivate each of the functional modules and program the unified value using the external system.

20 Claims, 7 Drawing Sheets

ANTI-TACHYARRHYTHMIA SYSTEM WITH UNIFIED ATRIAL TACHYARRHYTHMIA RATE THRESHOLD

CROSS-REFERENCE TO RELATED APPLICATION

This application claims the benefit of U.S. Provisional Application No. 61/009,065, filed on Dec. 20, 2007, under 35 U.S.C. §119(e), which is hereby incorporated by reference.

TECHNICAL FIELD

This document relates generally to cardiac rhythm management (CRM) systems and particularly to an anti-tachyarrhythmia system with various tachyarrhythmia detection and therapy algorithms using a unified atrial tachyarrhythmia rate threshold.

BACKGROUND

Tachyarrhythmias are abnormal heart rhythms characterized by a rapid heart rate. Tachyarrhythmia generally includes supraventricular tachyarrhythmia and ventricular tachyarrhythmia. Fibrillation is a form of tachyarrhythmia further characterized by an irregular heart rhythm. In a normal heart, the sinoatrial (SA) node, the heart's predominant natural pacemaker, generates electrical impulses, called action potentials, that propagate through an electrical conduction system to the atria and then to the ventricles of the heart to excite the myocardial tissues. The atria and ventricles contract in the normal atrio-ventricular sequence and synchrony to result in efficient blood-pumping functions indicated by a normal hemodynamic performance. Ventricular tachyarrhythmia occurs when the electrical impulses propagate along a pathologically formed self-sustaining conductive loop within the ventricles or when a biologic pacemaker (focus) in a ventricle usurps control of the heart rate from the SA node. When the atria and the ventricles become dissociated during ventricular tachyarrhythmia, the ventricles may contract before they are properly filled with blood, resulting in diminished blood flow throughout the body. This condition becomes life-threatening when the brain is deprived of sufficient oxygen supply. Ventricular fibrillation (VF), in particular, stops blood flow within seconds and, if not timely and effectively treated, causes immediate death. In very few instances a heart recovers from VF without treatment.

Ventricular cardioversion and defibrillation are used to terminate most ventricular tachyarrhythmias, including ventricular tachycardia (VT), and VF. An implantable cardioverter defibrillator (ICD) is a CRM device that delivers cardioversion/defibrillation pulses, each being an electric shock, to terminate a detected tachyarrhythmia episode by depolarizing the entire myocardium simultaneously and rendering it refractory. An ICD typically also delivers another type of electrical therapy for tachyarrhythmia known as anti-tachycardia pacing (ATP). In ATP, the heart is competitively paced in an effort to interrupt the reentrant loop causing the tachyarrhythmia.

An ICD typically includes pacing and cardioversion/defibrillation capabilities. In addition to anti-tachyarrhythmia therapies including ATP and cardioversion/defibrillation, the ICD may also deliver chronic pacing therapies such as bradycardia pacing therapy and cardiac resynchronization therapy. A detected tachyarrhythmia episode triggers several responses in the ICD, such as classification of the tachyarrhythmia episode and delivery of one or more anti-tachyarrhythmia therapies based on the classification, and termination or adjustment of bradycardia pacing therapy or cardiac resynchronization therapy. Such responses are typically functional features of the ICD that are controllable by a user such as a physician or other caregiver. While patients are potentially benefiting from increased functional features of modern ICDs, there is a need for simplifying the programming of these features to facilitate their proper utilization.

SUMMARY

A CRM system includes an ICD and an external system. The ICD includes a plurality of functional modules performing tachyarrhythmia classification and therapy control functions using atrial tachyarrhythmia rate thresholds that are set to a unified value. In one embodiment, the CRM system allows a user to activate and deactivate each of the functional modules and program the unified value using the external system.

In one embodiment, an ICD includes a cardiac sensing circuit, a rate detector, a plurality of functional modules, and a threshold circuit. The cardiac sensing circuit senses one or more cardiac signals including an atrial electrogram. The rate detector detects an atrial rate from the atrial electrogram. The functional modules are each activated and deactivated, in response to a selection command, to perform a tachyarrhythmia classification or therapy control function using the atrial rate and an atrial tachyarrhythmia rate threshold. The threshold circuit receives a unified threshold value and sets the atrial tachyarrhythmia rate threshold for each activated functional module of the plurality of functional modules to the unified threshold value.

In one embodiment, a method for operating a CRM system is provided. One or more cardiac signals including an atrial electrogram are sensed. An atrial rate is detected from the atrial electrogram. One or more features of a plurality of functional features are activated in response to a selection command. The functional features are each associated with a tachyarrhythmia classification or therapy control function of an ICD performed using the atrial rate and an atrial tachyarrhythmia rate threshold. The atrial tachyarrhythmia rate threshold for each of the activated one or more features is set to a received unified threshold value.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
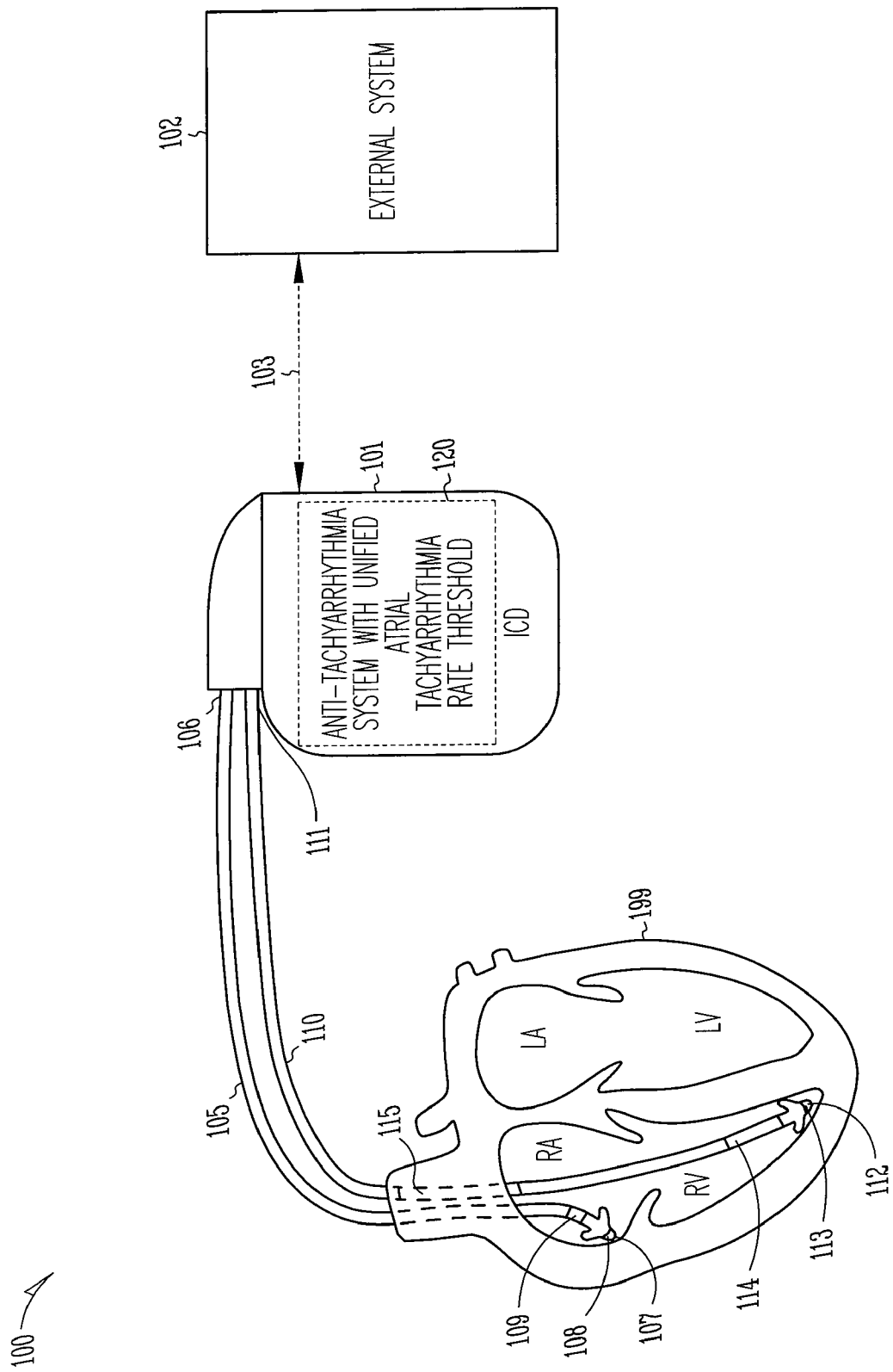
FIG. 1 is an illustration of an embodiment of a CRM system and portions of the environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this document are not necessarily to the same embodiment, and such references contemplate more than one embodiment.

The relationship between a heart rate and a cardiac cycle length (also known as cardiac interval), as used in this document, is the relationship between a frequency and its corresponding period. If a heart rate is given in beats per minute (bpm), its corresponding cardiac cycle length in milliseconds is calculated by dividing 60,000 by the heart rate (where 60,000 is the number of milliseconds in a minute). Any process, such as a comparison, using a heart rate is to be modified accordingly when a cardiac cycle length is used instead. For example, if a tachyarrhythmia is detected when the ventricular rate exceeds a tachyarrhythmia threshold rate (also referred to as rate threshold), an equivalent process is to detect the tachyarrhythmia when the ventricular cycle length (also known as ventricular interval) falls below a tachyarrhythmia threshold interval (also referred to as interval threshold). The appended claims should be construed to cover such variations.

In this document, a "fast beat" refers to a heart beat having a heart rate that falls into a tachyarrhythmia detection zone, which is typically defined by at least one tachyarrhythmia detection threshold, and a "slow beat" refers to a heart beat having a heart rate that is below the tachyarrhythmia detection zone. In other words, a "fast beat" is a heart beat having a heart rate that is considered tachyarrhythmic, and a "slow beat" is a heart beat having a heart rate that is not considered tachyarrhythmic.

This document discusses, among other things, a CRM system that includes an ICD having a plurality of functional modules that use a unified atrial tachyarrhythmia rate threshold. In various embodiments, these functional modules perform tachyarrhythmia classification and/or therapy control functions that depend on whether the patient's atrial rate exceeds the atrial tachyarrhythmia rate threshold, or equivalently, whether the patient's atrial interval is shorter than the atrial tachyarrhythmia interval threshold. These functional modules each use a parameter that is set to, or derived from, the atrial tachyarrhythmia rate threshold or the atrial tachyarrhythmia interval threshold. In one embodiment, the atrial tachyarrhythmia rate threshold is referred to as an atrial fibrillation (AF) rate threshold. AF is considered to be present when the patent's atrial rate exceeds the AF rate threshold.

FIG. 1 is an illustration of an embodiment of a CRM system 100 and portions of the environment in which CRM system 100 operates. CRM system 100 includes an ICD 101 that is electrically coupled to a heart 199 through leads 105 and 110. An external system 102 communicates with ICD 101 via a telemetry link 103.

ICD 101 is an implantable medical device that performs CRM functions including delivery of cardiac pacing and cardioversion/defibrillation therapies. ICD 101 includes a hermetically sealed can housing an electronic circuit that senses physiological signals and delivers therapeutic electrical pulses. The hermetically sealed can may also function as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 is typically a pacing lead that includes a proximal end 106 connected to ICD 101 and a distal end 107 placed in the right atrium (RA) of heart 199. A pacing-sensing electrode 108 is located at distal end 107. Another pacing-sensing electrode 109 is located near distal end 107. Electrodes 108 and 109 are electronically connected to ICD 101 via separate conductors in lead 105 to allow for sensing of the atrial electrogram and/or delivery of atrial pacing pulses. Lead 110 is typically a defibrillation lead that includes a proximal end 111 connected to ICD 101 and a distal end 112 placed in the right ventricle (RV) of heart 199. A pacing-sensing electrode 113 is located at distal end 112. A defibrillation electrode 114 is located near distal end 112 but electrically separated from pacing-sensing electrode 113. Another defibrillation electrode 115 is located at a distance from distal end 112 for supraventricular placement. Electrodes 113, 114, and 115 are electrically connected to ICD 101 via separate conductors in lead 110. Electrode 113 and 114 allow for sensing of the ventricular electrogram and/or delivery of ventricular pacing pulses. Electrodes 114 and 115 allow for delivery of ventricular cardioversion/defibrillation pulses. The functions of these electrodes are discussed above by way of example and not by way of limitation. Other ways of using these electrodes are possible as understood by those of skill in the art.

ICD 101 includes an anti-tachyarrhythmia system 120 that uses a unified atrial tachyarrhythmia rate threshold. Anti-tachyarrhythmia system 120 includes a plurality of functional modules each configured to be activated and deactivated by programming ICD 101 through external system 102. The functional modules each use an atrial tachyarrhythmia rate threshold that is set to a unified value. In one embodiment, this unified value is programmable by the user using external system 102. Anti-tachyarrhythmia system 120 is further discussed below, with references to FIGS. 2-5.

External system 102 allows for programming of ICD 101 and receives signals acquired by ICD 101. The programming of ICD 101 includes the selection of the functional modules and the programming of the unified value for the atrial tachyarrhythmia rate threshold, as further discussed below, with references to FIGS. 5 and 6. In one embodiment, external system 102 includes a programmer. In another embodiment, external system 102 is a patient management system including an external device in proximity of ICD 101, a remote device in a relatively distant location, and a telecommunication network linking the external device and the remote device. The patient management system provides for access to ICD 101 from a remote location, such as for monitoring patient status and/or adjusting therapies. In one embodiment, telemetry link 103 is an inductive telemetry link. In an alternative embodiment, telemetry link 103 is a far-field radio-frequency telemetry link. Telemetry link 103 provides for data transmission from ICD 101 to external system 102. This may include, for example, transmitting real-time physiological data acquired by ICD 101, extracting physiological data acquired by and stored in ICD 101, extracting therapy history data stored in ICD 101, and extracting data indicating an operational status of ICD 101 (e.g., battery status and lead impedance). Telemetry link 103 also provides for data transmission from external system 102 to ICD 101. This may include, for example, programming ICD 101 to acquire physiological data, programming ICD 101 to perform at least one self-diagnostic test (such as for a device operational status), programming ICD 101 to run a signal analysis algorithm (such as an algorithm implementing a tachyarrhythmia classification method discussed in this document), and programming ICD 101 to deliver pacing and/or cardioversion/defibrillation therapies.

The circuit of ICD 101, including its various elements discussed in this document, may be implemented using a combination of hardware and software. In various embodiments, each element of ICD 101 discussed in this document may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof. For example, a "comparator" includes, among other things, an electronic circuit comparator constructed to perform the only function of a comparison between two signals or a portion of a general-purpose circuit driven by a code instructing that portion of the general-purpose circuit to perform the comparison between the two signals.

Figure 2:
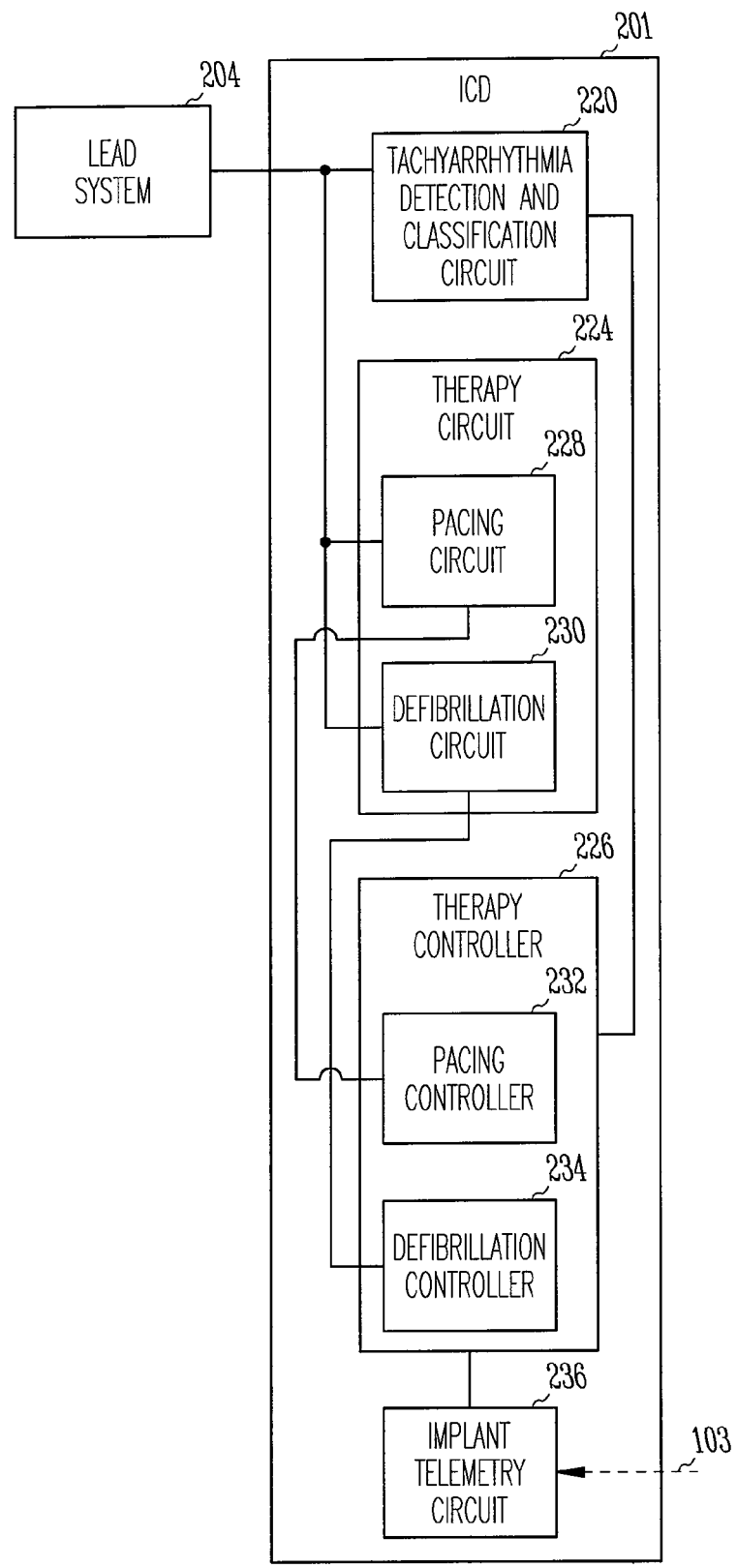
FIG. 2 is a block diagram illustrating an embodiment of the ICD and a lead system of the CRM system.

FIG. 2 is a block diagram illustrating an embodiment of an ICD 201 and a lead system 204. Lead system 204 includes one or more leads such as leads 105 and 110. ICD 201 is a specific embodiment of ICD 101 and includes a tachyarrhythmia detection and classification circuit 220, a therapy circuit 224, a therapy controller 226, and an implant telemetry circuit 236. Tachyarrhythmia detection and classification circuit 220 detects and classifies tachyarrhythmia episode using at least one or more intrinsic electrical cardiac signals sensed using lead system 204. In one embodiment, in addition to one or more cardiac signals, tachyarrhythmia detection and classification circuit 220 uses one or more other physiological signals, such as one or more signals indicative of hemodynamic performance, to detect and classify tachyarrhythmia episode. Therapy circuit 224 includes a pacing circuit 228 to deliver pacing pulses to heart 199 through lead system 204 and a defibrillation circuit 230 to deliver cardioversion/defibrillation pulses to heart 199 through lead system 204. Therapy controller 226 includes a pacing controller 232 to control the delivery of the pacing pulses, including ATP pulses, and a defibrillation controller 234 to control the delivery of the cardioversion/defibrillation pulses. Therapy controller 226 selects one or more of pacing and cardioversion/defibrillation therapies based on the classification of the tachyarrhythmia episode. In one embodiment, an ATP therapy is delivered when a detected tachyarrhythmia is classified as a type of tachyarrhythmia known to be treatable by the ATP therapy. If the ATP therapy fails to terminate the tachyarrhythmia, a cardioversion/defibrillation therapy is delivered. Implant telemetry circuit 236 allows ICD 201 to communicate with external system 102 via telemetry link 103.

Figure 3:
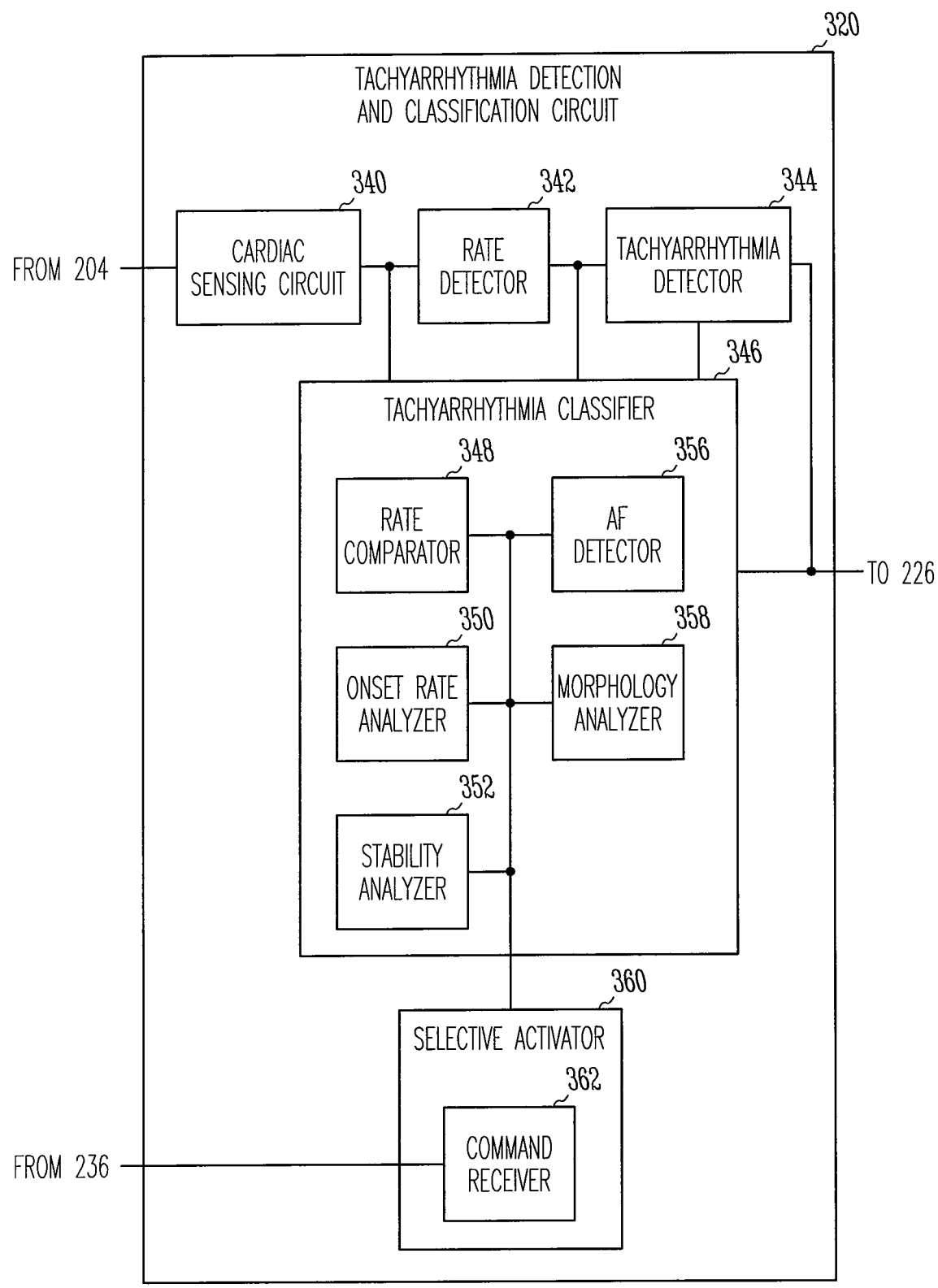
FIG. 3 is a block diagram illustrating an embodiment of a tachyarrhythmia detection and classification circuit of the ICD.

FIG. 3 is a block diagram illustrating an embodiment of a tachyarrhythmia detection and classification circuit 320. Tachyarrhythmia detection and classification circuit 320 is a specific embodiment of tachyarrhythmia detection and classification circuit 220 and includes a cardiac sensing circuit 340, a rate detector 342, a tachyarrhythmia detector 344, a tachyarrhythmia classifier 346, and selective activator detector 360.

Cardiac sensing circuit 340 senses one or more cardiac signals, such as one or more electrograms, through lead system 204. In one embodiment, cardiac sensing circuit 340 is electrically coupled to heart 199 through lead system 204 to sense an atrial electrogram and a ventricular electrogram from the heart. The atrial electrogram includes atrial events, also known as P waves, each indicative of an atrial depolarization. The ventricular electrogram includes ventricular events, also known as R waves, each indicative of a ventricular depolarization.

Rate detector 342 detects one or more heart rates from one or more cardiac signals sensed by cardiac sensing circuit 340. In one embodiment, rate detector 342 detects an atrial rate from the atrial electrogram and a ventricular rate from the ventricular electrogram. The atrial rate is the frequency of the atrial events. The ventricular rate is the frequency of the ventricular events. In one embodiment, the atrial and ventricular rates are each expressed in beats per minute (bpm), i.e., number of detected atrial or ventricular depolarizations per minute.

Tachyarrhythmia detector 344 detects a tachyarrhythmia episode. In one embodiment, a tachyarrhythmia is detected when the ventricular rate exceeds a predetermined tachyarrhythmia threshold rate. In one embodiment, tachyarrhythmia detector 344 detects tachyarrhythmia by determining whether the ventricular rate is within one of a plurality of tachyarrhythmia rate zones each including a predetermined threshold rate. In a specific embodiment, the plurality of tachyarrhythmia rate zones includes a VF rate zone with a VF threshold rate programmable between 130 and 250 bpm, a fast VT rate zone with a fast VT threshold rate programmable between 110 and 210 bpm, and a slow VT rate zone with a slow VT threshold rate programmable between 90 and 200 bpm.

Tachyarrhythmia classifier 346 classifies each tachyarrhythmia detected by tachyarrhythmia detector 344. Examples of classification of tachyarrhythmia made by tachyarrhythmia classifier 346 include ventricular fibrillation (VF), ventricular tachycardia (VT), and supraventricular tachycardia (SVT), which includes atrial fibrillation (AF), atrial flutter (AFL), sinus tachycardia (ST), and atrial tachycardia (AT). An example of such tachyarrhythmia classifier providing for classification of VF, VT, SVT, AF, AFL, ST, and AT is discussed in U.S. Provisional Patent Application Ser. No. 60/978,972, "METHOD AND APPARATUS FOR CONCURRENT ATRIO-VENTRICULAR ANTI-TACHYCARDIA PACING", filed on Oct. 10, 2007, assigned to Cardiac Pacemakers, Inc., which is incorporated herein by reference in its entirety.

In one embodiment, tachyarrhythmia classifier 346 stores a plurality of detection enhancements and includes a plurality of detection enhancement modules each configured perform one of the detection enhancements. In the illustrated embodiment, for example, the detection enhancement modules include a rate comparator 348, an onset rate analyzer 350, a stability analyzer 352, an atrial fibrillation (AF) detector 356, and a morphology analyzer 358. Selective activator 360 includes a command receiver 362 to receive from external system 102 a selection command including the classification mode selected by the user. The classification mode corresponds to a selection of none, one, or more of the detection enhancements. According to the selection, selective activator 360 activates none, one, or more of the detection enhancement modules used in the classification mode, and deactivates none, one, or more of the detection enhancement modules not used in the classification mode.

In one embodiment, in response to the detection of a tachyarrhythmia episode by tachyarrhythmia detector 344, tachyarrhythmia classifier 346 classifies the tachyarrhythmia episode as one of VT and SVT. In one embodiment, a VT classification triggers the delivery of a ventricular anti-tachyarrhythmia therapy including ventricular ATP and/or ventricular cardioversion/defibrillation, and an SVT therapy inhibits the delivery of the ventricular anti-tachyarrhythmia therapy.

Rate comparator 348 compares the atrial rate and the ventricular rate to determine whether the ventricular rate is substantially higher than the atrial rate. VT is indicated when the ventricular rate is higher than the atrial rate by a predetermined margin. In one embodiment, the predetermined margin is programmable by the user. In one embodiment, the predetermined margin is programmed to about 10 bpm.

Onset rate analyzer 350 produces an onset rate of the detected tachyarrhythmia and determines whether the detected tachyarrhythmia has a gradual onset or a sudden onset by comparing the onset rate to one or more threshold onset rates. The onset rate is a rate of transition of the ventricular rate from a normal sinus rate to a tachyarrhythmic rate when the detected tachyarrhythmia begins. A gradual onset typically indicates a physiological tachyarrhythmia, such as SVT caused by exercise. A sudden onset typically indicates a pathological tachyarrhythmia.

Stability analyzer 352 produces a rate stability parameter indicative of a degree of heart rate variability and determines whether the heart rate is stable by comparing the stability parameter to a stability threshold. An unable ventricular stability is an indication of SVT. In one embodiment, a rate stability parameter is produced as an average difference between consecutive ventricular intervals. Stability analyzer 352 determines whether the ventricular rate is stable by comparing the rate stability parameter to the stability threshold. In one embodiment, the stability threshold is programmed by the user. In one embodiment, the stability threshold is programmable between 6 ms and 120 ms.

AF detector 356 compares the atrial rate to an AF rate threshold and declares a detection of AF (a type of SVT) if the atrial rate exceeds the AF rate threshold. In one embodiment, the AF rate threshold is programmed by the user. In one embodiment, the AF rate threshold is programmable between 200 bpm and 400 bpm. In one embodiment, the AF rate threshold is set to the unified value of the atrial tachyarrhythmia rate threshold.

Morphology analyzer 358 analyzes a correlation between a tachyarrhythmic waveform and a template waveform and produces a correlation coefficient representative of that correlation. The tachyarrhythmic waveform includes a segment of a cardiac signal sensed during the detected tachyarrhythmia. The template waveform is recorded during a known cardiac rhythm such as the normal sinus rhythm (NSR). One example for producing such a correlation coefficient, referred to as a feature correlation coefficient (FCC), is discussed in U.S. Pat. No. 6,708,058, "NORMAL CARDIAC RHYTHM TEMPLATE GENERATION SYSTEM AND METHOD," assigned to Cardiac Pacemakers, Inc., which is hereby incorporated in its entirety. In one embodiment, the detected tachyarrhythmia is considered as "correlated", which indicates SVT, if a correlation coefficient exceeds a correlation threshold.

Figure 4:
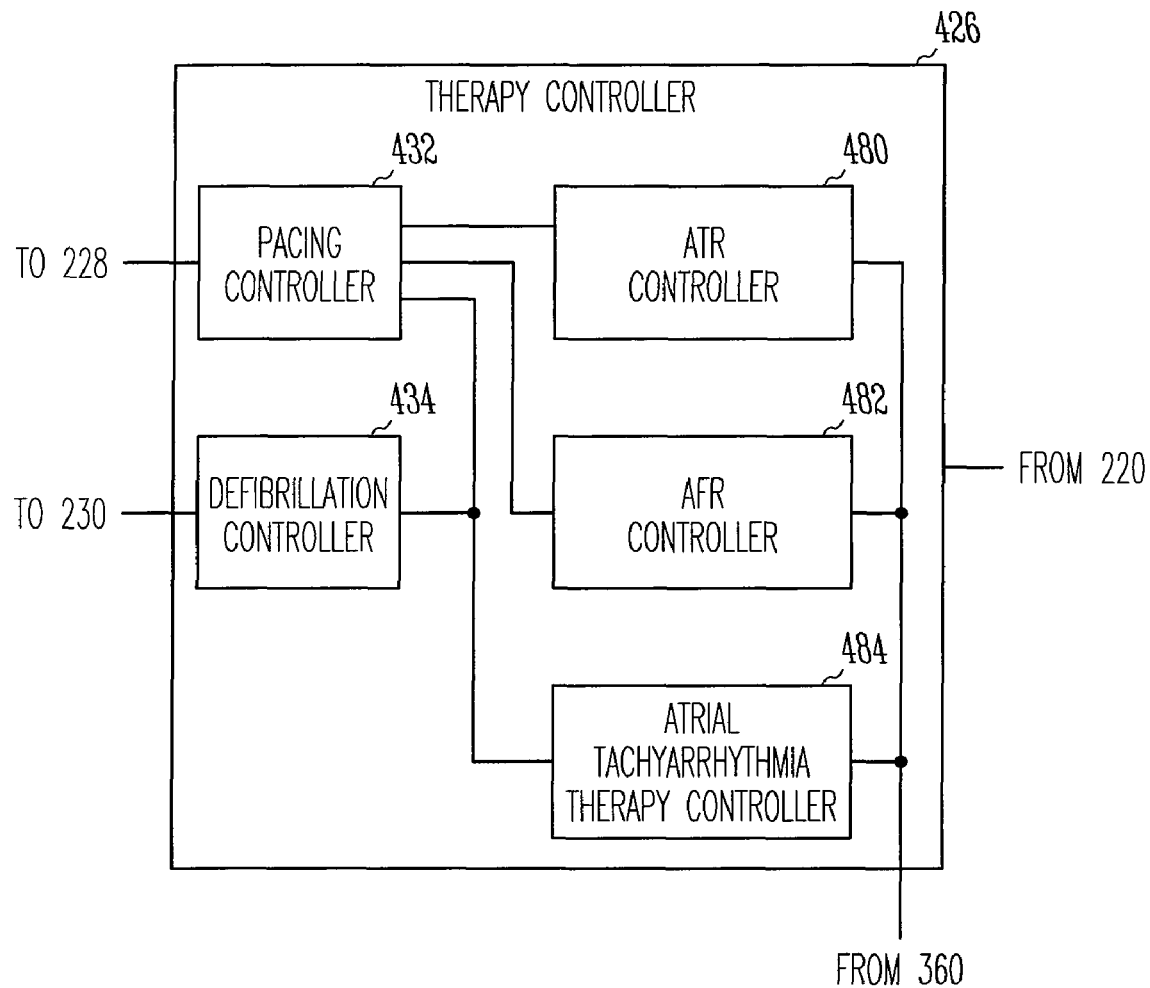
FIG. 4 is a block diagram illustrating an embodiment of a therapy controller of the ICD.

FIG. 4 is a block diagram illustrating an embodiment of a therapy controller 426. Therapy controller 426 is a specific embodiment of therapy controller 226 and includes a pacing controller 432, a defibrillation controller 434, an atrial tachyarrhythmia response (ATR) controller 480, an atrial flutter response (AFR) controller 482, and an atrial tachyarrhythmia therapy controller 484. Pacing controller 432 controls the delivery of the pacing pulses, including ATP and other pacing pulses. Defibrillation controller 434 controls the delivery of the cardioversion/defibrillation pulses. In one embodiment, selective activator 360 also activates and deactivates each of ATR controller 480, AFR controller 482, and atrial tachyarrhythmia therapy controller 484 according to the selection command.

ATR controller 480 controls delivery of pacing pulses using an ATR rate. When the atrial rate of the patient exceeds the ATR rate, ATR controller 480 adjusts the delivery of pacing pulses, such as by switching to a different pacing mode. In one embodiment, the ATR rate is an atrial tachyarrhythmia rate threshold above which sensed atrial events are considered not suitable for controlling delivery of pacing in an atrial tracking mode. For example, when the atrial rate of the patient exceeds the ATR rate, ATR controller 480 switches a pacing mode from DDD to VVI, VDI, or DDI, or from VDD to VDI. The DDD, VDD, VVI, VDI, and DDI include their rate-responsive versions: DDDR, VDDR, VVIR, VDIR, and DDIR, respectively. In one embodiment, the ATR rate is set to the unified value of the atrial tachyarrhythmia rate threshold.

AFR controller 482 controls the detection of intrinsic atrial depolarizations that trigger the delivery of ventricular pacing pulses during an atrial tracking pacing mode. In one embodiment, if an intrinsic atrial depolarization is detected during a post-ventricular atrial refractory period (PVARP), the intrinsic atrial depolarization triggers an AFR window that functions as an extension of the PVARP. The AFR window is retriggerable. If a second intrinsic atrial depolarization is detected during the AFR window triggered by a first intrinsic atrial depolarization, the second intrinsic atrial depolarization restarts the AFR window. In one embodiment, the AFR window is set to an interval value that corresponds to the unified value of the atrial tachyarrhythmia rate threshold. That is, the AFR window is set to equal to the atrial tachyarrhythmia interval threshold corresponding to the atrial tachyarrhythmia rate threshold.

Atrial tachyarrhythmia therapy controller 484 controls the delivery of atrial ATP and/or atrial cardioversion/defibrillation therapies when such therapies are available from ICD 201. When the atrial rate exceeds an atrial tachyarrhythmia therapy rate, the atrial ATP and/or atrial cardioversion/defibrillation therapies are delivered from pacing circuit 228 and/or defibrillation circuit 230. In one embodiment, the atrial tachyarrhythmia therapy rate is set to the unified value of the atrial tachyarrhythmia rate threshold.

Figure 5:
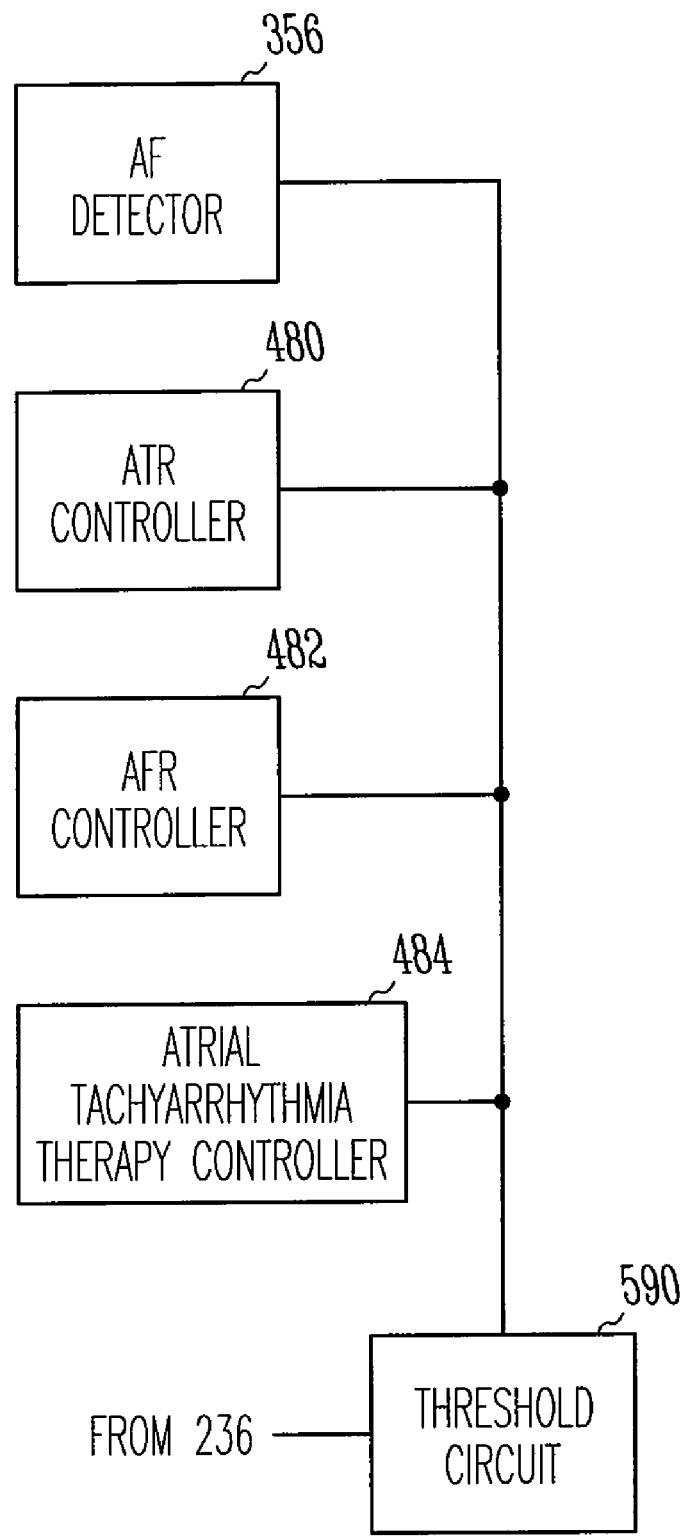
FIG. 5 is a block diagram illustrating an embodiment of functional modules of the ICD that uses a unified atrial tachyarrhythmia rate threshold.

FIG. 5 is a block diagram illustrating an embodiment of functional modules in ICD 201 that use the unified value of the atrial tachyarrhythmia rate threshold. In the illustrated embodiment, the functional modules include AF detector 356, ATR controller 480, AFR controller 482, and atrial tachyarrhythmia therapy controller 484, as discussed above with reference to FIGS. 3 and 4. In various other embodiments, the functional modules includes any one or more of AF detector 356, ATR controller 480, AFR controller 482, and atrial tachyarrhythmia therapy controller 484 as well as one or more functional modules providing for other tachyarrhythmia classification and therapy features. A threshold circuit 590 provides each of these functional modules, if activated, with the unified value of the atrial tachyarrhythmia rate threshold or the corresponding interval value. In one embodiment, threshold circuit 590 includes a storage device that stores the unified value of the atrial tachyarrhythmia rate threshold and/or the corresponding interval value. In one embodiment, threshold circuit 590 receives the unified value from external system 102 and updates the stored unified value of the atrial tachyarrhythmia rate threshold and/or the corresponding interval value.

Figure 6:
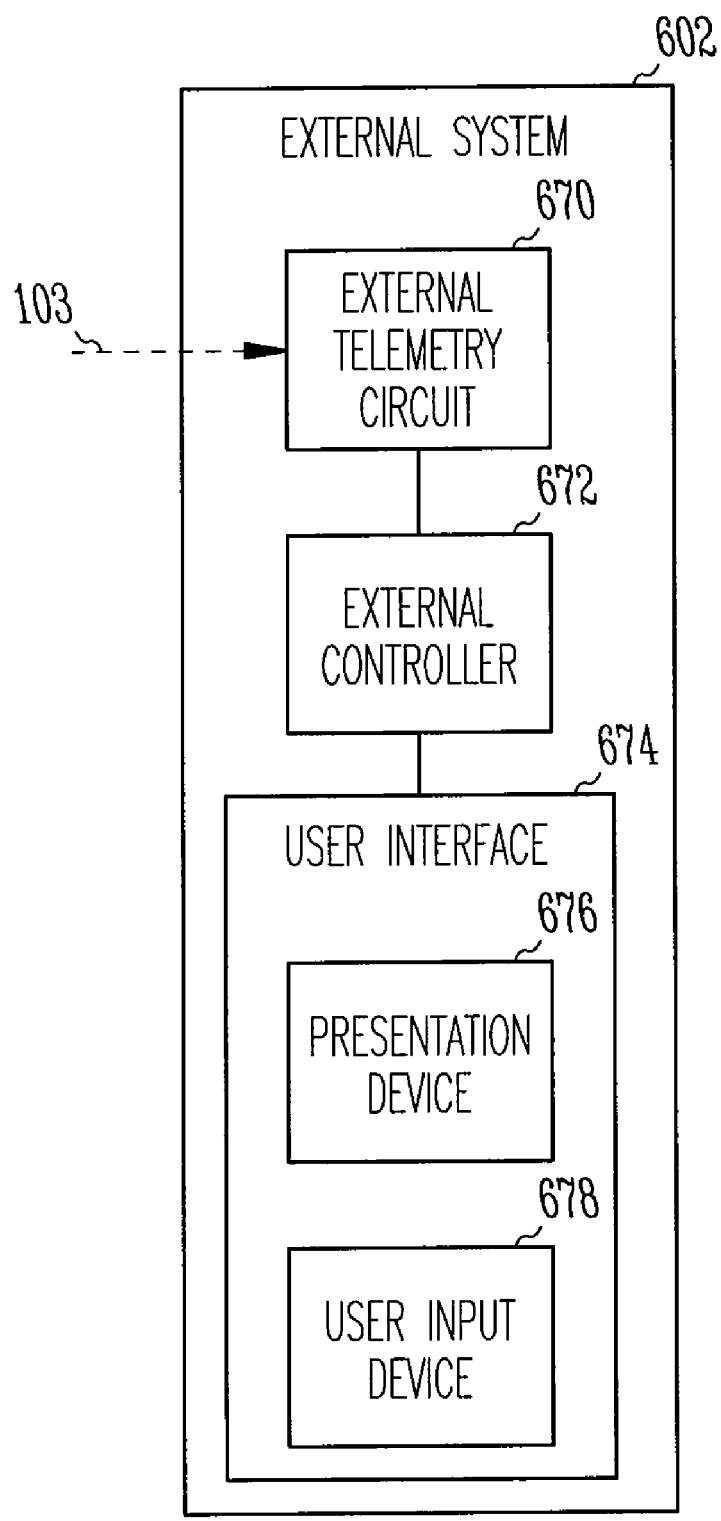
FIG. 6 is a block diagram illustrating an embodiment of an external system of the CRM system.

FIG. 6 is a block diagram illustrating an embodiment of an external system 602. External system 602 is a specific embodiment of external system 102 and includes an external telemetry circuit 670, an external controller 672, and a user interface 674. External telemetry circuit 670 allows external system 602 to communicate with ICD 101 via telemetry link 103. External controller 672 controls the operations of external system 602, including the programming of ICD 101. User interface 674 allows the user to interact with the CRM system, including programming of ICD 101 and monitoring operation status of ICD 101 and condition of the patient in whom ICD 101 is implanted. In the illustrated embodiment, user interface 674 includes a presentation device 676 and a user input device 678. To allow the user to select functional features, for example, presentation device 676 presents the feature provided by each of AF detector 356, ATR controller 480, AFR controller 482, and atrial tachyarrhythmia therapy controller 484, and user input device 478 receives the user selection of the features as well as the unified value of the atrial tachyarrhythmia rate threshold. In one embodiment, an interactive screen functions as part of both presentation device 676 and user input device 678. After receiving the user selection, external controller 672 produces the selection command including the selected features and programs ICD 101 by transmitting the selection command and the unified value of the atrial tachyarrhythmia rate threshold to ICD 101 via telemetry link 103.

Figure 7:
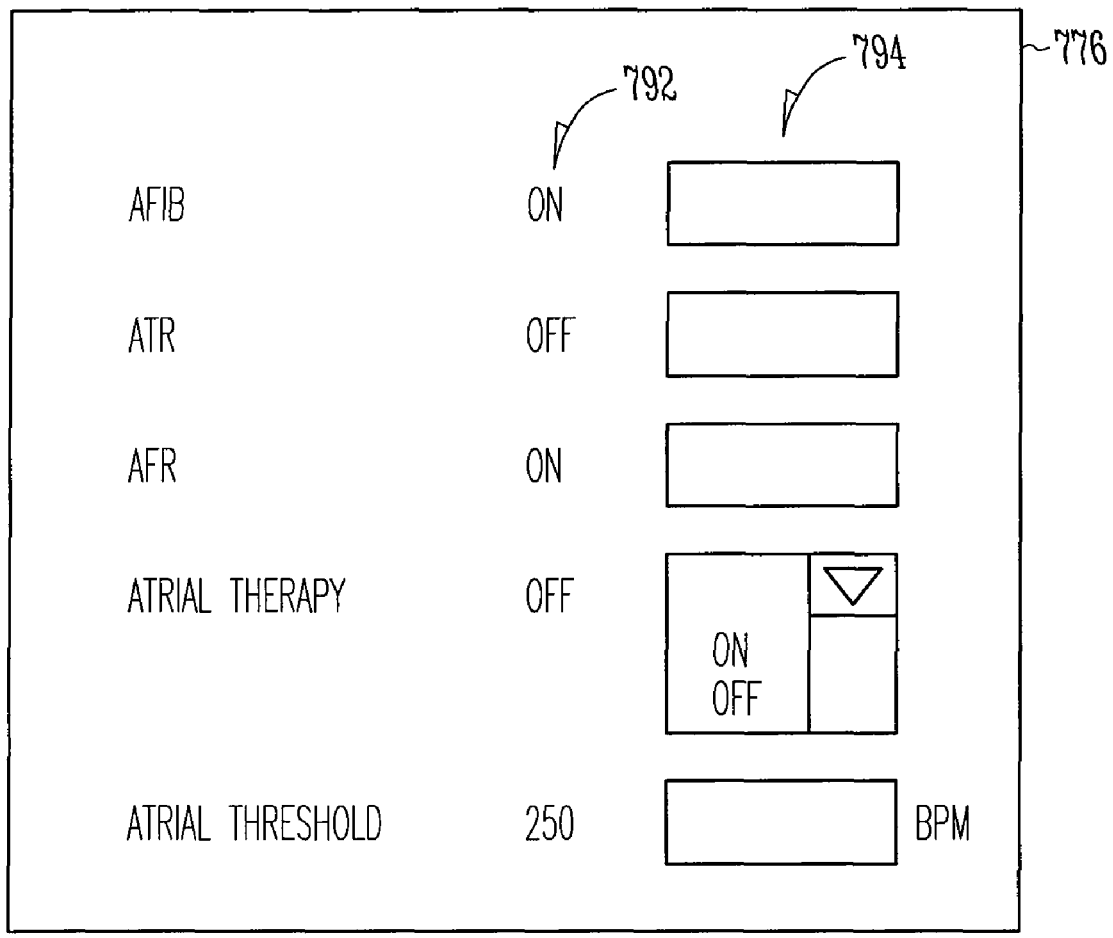
FIG. 7 is an illustration of an embodiment of portions of a screen of a user interface of the external system.

FIG. 7 is an illustration of an embodiment of portions of a screen 776, which is a specific embodiment of presentation device 676. In the illustrated embodiment, screen 776 displays the feature provided by each of AF detector 356 (AFIB), ATR controller 480 (ATR), AFR controller 482 (AFR), and atrial tachyarrhythmia therapy controller 484 (Atrial Therapy), including their activation status 792 (ON or OFF) followed by a programming field 794 that allows the user to change the status by selecting ON to activate or OFF to deactivate each of these features. Screen 776 further displays the unified value of the atrial tachyarrhythmia rate threshold (Atrial Threshold), including its current value as current status 792 following by programming field 794 that allows the user to adjust the value. In one embodiment, the atrial tachyarrhythmia rate threshold is programmable in the range of 200 bpm to 400 bpm.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A cardiac rhythm management (CRM) system, comprising:
   an implantable cardioverter defibrillator (ICD) including:
   a cardiac sensing circuit configured to sense one or more cardiac signals including an atrial electrogram;
   a rate detector configured to detect an atrial rate from the atrial electrogram;
   a plurality of functional modules each configured to be activated and deactivated in response to a selection command, the functional modules each performing a tachyarrhythmia classification or therapy control function using the atrial rate and an atrial tachyarrhythmia rate threshold; and
   a threshold circuit configured to receive a unified threshold value and set the atrial tachyarrhythmia rate threshold for each activated functional module of the plurality of functional modules to the unified threshold value.

2. The system of claim 1, wherein the plurality of functional modules comprises an atrial fibrillation (AF) detector configured to compare the atrial rate to an AF rate threshold and declare a detection of AF in response to the atrial rate exceeding the AF rate threshold, wherein the threshold circuit is configured to set the AF rate threshold to the unified threshold value.

3. The system of claim 1, wherein the plurality of functional modules comprises an atrial tachyarrhythmia response (ATR) controller configured to adjust delivery of pacing pulses in response to the atrial rate exceeding an ATR rate, wherein the threshold circuit is configured to set the ATR rate to the unified threshold value.

4. The system of claim 3, wherein the ATR controller is configured to switch a pacing mode in response to the atrial rate exceeding the ATR rate.

5. The system of claim 4, wherein the ATR controller is configured to switch the pacing mode from DDD mode to VVI, DDI, or VDI mode, or from VDD mode to VDI mode, in response to the atrial rate exceeding the ATR rate.

6. The system of claim 1, wherein the plurality of functional modules comprises an atrial flutter response (AFR) controller configured to trigger an AFR window in response to a detection of an intrinsic atrial depolarization, the AFR window used for controlling detection of intrinsic atrial depolarizations that trigger delivery of ventricular pacing pulses during an atrial tracking pacing mode, wherein the threshold circuit is configured to set the AFR window to an atrial tachyarrhythmia interval value corresponding to the unified threshold value.

7. The system of claim 6, wherein the AFR controller is configured to retrigger the AFR window in response to a detection of the intrinsic atrial depolarization during the AFR window.

8. The system of claim 1, wherein the plurality of functional modules comprises an atrial tachyarrhythmia therapy controller configured to cause delivery of an anti-tachyarrhythmia therapy in response to the atrial rate exceeding an atrial tachyarrhythmia therapy rate, wherein the threshold circuit is configured to set the atrial tachyarrhythmia therapy rate to the unified threshold value.

9. The system of claim 1, comprising an external system configured to be communicatively coupled to the ICD via telemetry, the external system including a user input device configured to receive the unified threshold value.

10. The system of claim 9, wherein the external system comprises an external controller configured to produce the selection command using a user selection of one or more features from a plurality of features provided by the plurality of functional modules, and wherein the user input device is configured to receive the user selection.

11. A method for operating a cardiac rhythm management (CRM) system, the method comprising:
sensing one or more cardiac signals including an atrial electrogram;
detecting an atrial rate from the atrial electrogram;
activating one or more features of a plurality of functional features in response to a selection command, the functional features each associated with a tachyarrhythmia classification or therapy control function of an implantable cardioverter defibrillator (ICD) performed using the atrial rate and an atrial tachyarrhythmia rate threshold;
receive a unified threshold value; and
setting the atrial tachyarrhythmia rate threshold for each of the activated one or more features to the unified threshold value.

12. The method of claim 11, comprising:
setting an atrial fibrillation (AF) rate threshold to the unified threshold value;
comparing the atrial rate to the AF rate threshold; and
declaring a detection of AF in response to the atrial rate exceeding the AF rate threshold.

13. The method of claim 11, comprising:
setting an atrial tachyarrhythmia response (ATR) rate to the unified threshold value; and
adjusting delivery of pacing pulses in response to the atrial rate exceeding the ATR rate.

14. The method of claim 13, wherein adjusting the delivery of pacing pulses comprises switching from a first pacing mode to a second pacing mode in response to the atrial rate exceeding the ATR rate.

15. The method of claim 11, comprising:
setting an atrial flutter response (AFR) window to an atrial tachyarrhythmia interval value corresponding to the unified threshold value; and
triggering the AFR window in response to a detection of an intrinsic atrial depolarization,
wherein the AFR window is used to control detection of intrinsic atrial depolarizations that trigger delivery of ventricular pacing pulses during an atrial tracking pacing mode.

16. The method of claim 15, comprising retriggering the AFR window in response to a detection of another intrinsic atrial depolarization during the AFR window.

17. The method of claim 11, comprising:
setting an atrial tachyarrhythmia therapy rate to the unified threshold value; and
delivering an anti-tachyarrhythmia therapy in response to the atrial rate exceeding the atrial tachyarrhythmia therapy rate.

18. The method of claim 11, comprising receiving the unified threshold value from a user using a user interface device of a programmer configured to communicate with the ICD via telemetry.

19. The method of claim 18, comprising displaying a user-changeable activation status for each feature of the plurality of functional features on an interactive screen of the user interface device, and producing the selection command according to the activation status for the each feature of the plurality of functional features.

20. The method of claim 19, comprising displaying the unified threshold value following by a programming field on the interactive screen, the programming field allowing the unified threshold value to be programmed to a value between 200 beats per minute and 400 beats per minute.

* * * * *